(12) United States Patent
Mulholland et al.

(10) Patent No.: US 10,039,288 B2
(45) Date of Patent: Aug. 7, 2018

(54) PATHOGENIC INFECTIONS

(71) Applicants: University of Surrey, Guildford, Surrey (GB); Forschungsinstitut Fur Biologischen Landbau (FiBL), Frick (CH)

(72) Inventors: Dulcie Mulholland, Guildford (GB); Moses Langat, Guildford (GB); Lucius Tamm, Elfingen (CH); Hansjacob Schaerer, Zeiningen (CH); Heikki Matti Tapio Hokkanen, Inkoo (FI); Ingeborg Marianne Menzier-Hokkanen, Kangasniemi (FI)

(73) Assignees: UNIVERSITY OF SURREY, Guildford, Surrey (GB); FORSCHUNGSINSTITUT FUR BIOLOGISCHEN LANDBAU (FIBL), Frick (CH)

( * ) Notice: Subject to any disclaimer, the term of this patent is extended or adjusted under 35 U.S.C. 154(b) by 82 days.

(21) Appl. No.: 15/265,796

(22) Filed: Sep. 14, 2016

(65) Prior Publication Data

US 2017/0000136 A1 Jan. 5, 2017

Related U.S. Application Data

(63) Continuation of application No. PCT/GB2015/050766, filed on Mar. 17, 2015.

(51) Int. Cl.
| | | |
|---|---|---|
| *A61K 36/00* | (2006.01) |
| *A01N 65/06* | (2009.01) |
| *A01N 31/06* | (2006.01) |
| *A01N 43/08* | (2006.01) |
| *A01N 65/00* | (2009.01) |

(52) U.S. Cl.
CPC ............. *A01N 65/06* (2013.01); *A01N 31/06* (2013.01); *A01N 43/08* (2013.01); *A01N 65/00* (2013.01)

(58) Field of Classification Search
CPC ...................................................... A61K 36/00
USPC .......................................................... 424/725
See application file for complete search history.

(56) References Cited

U.S. PATENT DOCUMENTS

| | | | |
|---|---|---|---|
| 2008/0124414 A1 | 5/2008 | Willför et al. | |
| 2013/0287714 A1* | 10/2013 | Gohla | A61K 8/64 424/59 |

FOREIGN PATENT DOCUMENTS

JP H07 25719 1/1995

OTHER PUBLICATIONS

International Search Report and Written Opinion dated May 8, 2015, in International Application No. PCT/GB2015/050766, 12 pages.
Chen et al., "Synthesis and Fungiciadal Activity of Novel Types of Diterpenes", Chinese Journal of Organic Chemistry, Abstract Only, Mar. 28, 2010, 461-464.
Cohen et al., "Systemic Fungicides and the Control of Oomycetes", Annual Review of Phytopathology, vol. 24, No. 1, Sep. 1, 1986, 311-338.

\* cited by examiner

*Primary Examiner* — Michael V Meller
(74) *Attorney, Agent, or Firm* — Kilpatrick Townsend & Stockton LLP

(57) ABSTRACT

The invention relates to plant pathogenic infections, and to the treatment of oomycete pathogenic infections. The invention extends to novel antimicrobial compositions comprising inhibitors of oomycete pathogens, and their use in methods of treating or preventing infections with such pathogens, for example downy mildew of grapevine.

9 Claims, 1 Drawing Sheet

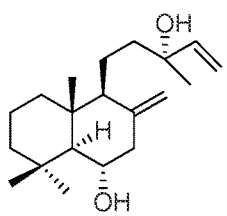
1. Larixol
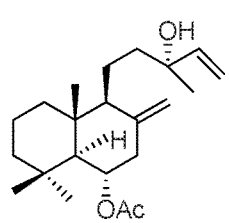
2. Larixyl acetate
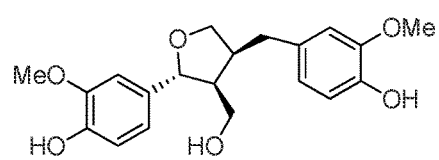
3. (+)-lariciresinol
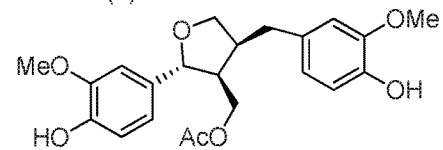
4. (+)-lariciresinol acetate

PATHOGENIC INFECTIONS

This application is a continuation of international application No. PCT/GB2015/050766, filed Mar. 17, 2015, which claims priority to United Kingdom application No. 1404848.2, filed Mar. 18, 2014, which are hereby incorporated by reference herein in their entirety.

The invention relates to pathogenic infections, especially plant pathogenic infections, and particularly, although not exclusively, to the treatment of oomycete pathogenic infections. The invention extends to novel antimicrobial compositions comprising inhibitors of oomycete pathogens, and their use in methods of treating or preventing infections with such pathogens, for example downy mildew of grapevine.

Downy mildew refers to any of several types of oomycete microbes that are parasites of plants. For example, *Plasmopara viticola* is a member of the oomycetes family and is a highly destructive disease of grapevines in all grape-growing areas of the world where there is spring and summer rainfall at temperatures above 10° C. Fungicides are the primary means of control in commercial grapevine production. Crop losses in individual years can be 100% if the disease is not controlled in weather favourable to the pathogen. Early infection of young grape bunches can lead to significant crop loss and leaf infection affects the source-sink relationship and may lead to defoliation and possible sunburn or lack of fruit ripening. This infection was first treated in 1885 using Bordeaux mixture (i.e. copper sulphate and lime) and this was the first example of chemical disease control.

In the pre-infection period, plants are sprayed with copper-based fungicides or synthetic agrochemicals, such as dithiocarbamates. Post infection treatments include fosetyl-aluminium and phenylamides (e.g. metalaxyl). In organic grape farming, the only treatments effective against *Plasmopara viticola* currently allowable under organic standards are based on copper hydroxide and copper sulphate. As a result of concerns about the environmental effects of heavy metals, such as copper, their use in organic farming is becoming more restricted. For example, in the European Union, organic standards allow a maximum of 6 kg/Ha per annum of copper.

Accordingly, there is a need to provide novel, environmentally friendly compositions for use in preventing pathogenic infections caused by microorganisms, for example downy mildew.

The inventors have produced a series of crude extracts from a variety of different *Larix* (i.e. larch) species, and found that several active compounds contained therein were surprisingly active against the oomycete *Plasmopara viticola*, i.e. the downy mildew-causing pathogen of grapevine.

Accordingly, in a first aspect of the invention, there is provided use of an extract from a *Larix* spp., for treating, preventing or reducing an oomycete pathogen infection.

As described in the examples, the plant extracts were surprisingly active against Grapevine downy mildew (i.e. *Plasmopara viticola*). Advantageously, therefore, the extracts and the active compounds contained therein present a novel, naturally occurring and environmentally friendly means for preventing microorganism-induced pathogenic infections, for example *Plasmopara viticola* in grapevine, or *Phytophthora infestans* in potato.

The *Larix* spp. plant extracts were separated using gravity column chromatography, and the active compounds, as determined by bioassays, were then identified using NMR spectroscopy. The inventors found four compounds, which exhibited the activity against oomycete pathogens, including: larixol, larixyl acetate (a naturally occurring acetate derivative of larixol), lariciresinol and lariciresinol acetate (a naturally occurring acetate derivative of lariciresinol). Lariciresinol and lariciresinol acetate are related lignins, and larixol and larixyl acetate are closely related diterpenoids.

Accordingly, preferably the plant extract comprises larixol or lariciresinol, or an active derivative thereof, most preferably an acetate derivative thereof. The inventors believe that this is an important feature of the invention.

Hence, in a second aspect, there is provided use of larixol or lariciresinol, or an active derivative thereof, for treating, preventing or ameliorating an oomycete pathogen infection.

Preferably, the pathogen infection is a plant pathogen caused by a micro-organism.

The inventors believe that they are the first to have produced a natural *Larix*-derived composition for treating or preventing infections of oomycete pathogens.

Accordingly, in a third aspect, there is provided an oomycete pathogen treatment composition comprising an extract from a *Larix* spp., or larixol or lariciresinol, or an active derivative thereof.

Advantageously, the composition does not comprise heavy metals, such as copper, and so is environmentally friendly, and can be described as being naturally occurring. It is therefore far superior than the compositions containing copper hydroxide and copper sulphate that are currently in use. The composition may be defined as being an agrochemical, which can be applied to the surface of an object at risk of infection by an oomycete pathogen.

Thus, in a fourth aspect, there is provided a method of treating, preventing or reducing an oomycete pathogen infection of an object, the method comprising contacting the object with an extract from a *Larix* spp., or larixol or lariciresinol, or an active derivative thereof.

The object may be already infected with an oomycete pathogen, or be at risk of being infected. The object may be any plant (e.g. fruit or vegetable, grapevine, ornamental plant), or a fruit or vegetable storage means or container. Preferably, the method of the fourth aspect comprises contacting the object with the composition of the third aspect.

The skilled person will appreciate that the compounds larixol and lariciresinol can be modified or derivatised to produce an active derivative, which exhibits antimicrobial activity against oomycetes, for example *Plasmopara viticola*. For example, in one preferred embodiment, the active derivative of larixol or lariciresinol comprises a labdane diterpenoid. In another preferred embodiment, the active derivative comprises a derivative of lignan. In yet another preferred embodiment, the active derivative comprises a synthetic derivative of any of the aforementioned compounds, such as other ester derivatives, heterocyclic derivatives and derivatives derived by alkylation or oxidation. In a most preferred embodiment, however, the active derivative of larixol or lariciresinol comprises larixyl acetate or lariciresinol acetate.

It should be appreciated that the active compounds isolated from the *Larix* spp. plant extracts have a number of synonyms, which also forms part of the invention. For example, larixol is also known as:—
1. 8(17),14-Labdadien-6α,13(S)-diol;
2. Labda-8(20),14-diene-6α,13-diol, (13S);
3. α-Ethenyldecahydro-4-hydroxy-α,5,5,8a-tetramethyl-2-methylene-1S-[1α(R*),4β,4aβ,8aα]]-1-naPhthalenepropanol; or
4. α-Eethenyldecahydro-4-hydroxy-α,5,5,8a-tetramethyl-2-methylene-(αS,1S,4S,4aS,8aR)-1-naphthalenepropanol.

Larixyl acetate is also known as:—
1. 4-(Acetyloxy)-α-ethenyldecahydro-α,5,5,8a-tetramethyl-2-methylene-(αS,1S,4S,4aS,8aR)-1-naphthalenepropanol;
2. 4-(Acetyloxy)-α-ethenyldecahydro-α,5,5,8a-tetramethyl-2-methylene-[1S-[1α(R*),4β,4aβ,8aα]]-1-naphthalenepropanol; or
3. Labda-8(20),14-diene-6α,13(S)-diol, 6-acetate.

Lariciresinol or (+)-lariciresinol (NSC 329247) is also known as:—
1. Tetrahydro-2-(4-hydroxy-3-methoxyphenyl)-4-[(4-hydroxy-3-methoxyphenyemethyl]-, (2S,3R,4R)-3-furanmethanol;
2. Tetrahydro-2-(4-hydroxy-3-methoxyphenyl)-4-[(4-hydroxy-3-methoxyphenyemethyl]-, [2S-(2α,3β, 4β)]-3-furanmethanol;
3. Tetrahydro-2-(4-hydroxy-3-methoxyphenyl)-4-vanillyl-3-Furanmethanol; or
4. (+)-4,4',9'-Trihydroxy-3,3'-dimethoxy-7',9-epoxylignan.

Lariciresinol acetate or (+)-lariciresinol acetate is also known as:—
1. Tetrahydro-2-(4-hydroxy-3-methoxyphenyl)-4-[(4-hydroxy-3-methoxyphenyemethyl]-3-acetate, (2S,3R, 4R)-3-furanmethanol; or
2. Tetrahydro-2-(4-hydroxy-3-methoxyphenyl)-4-[(4-hydroxy-3-methoxyphenyemethyl]-α-acetate (2S,3R, 4R)-3-furanmethanol.

The inventors have found that these active compounds are present in varying amounts depending on the *Larix* species from which they are derived. The genus *Larix* includes conifers belonging to the family Pinaceae. There is some disagreement on the number of species, as hybridisation occurs, but the *Plant List* produced by Missouri Botanical Gardens and the Royal Botanical Gardens, Kew lists 14 as accepted species names and 63 as synonyms (http://www.theplantlist.org/browse/G/Pinaceae/*Larix*/). Preferably, therefore, the plant extract or the active compound obtained from a *Larix* spp. is selected from the group consisting of: *L. czekanowskii; L. decidua; L. gmelinii; L. griffithii; L. kaempferi; L. laricina; Larix×lubarskii; L. lyallii; Larix× maritime; L. mastersiana; L. occidentalis; Larix×polonica; L. potaninii*; and *L. sibirica*.

More preferably, the plant extract or the active compound is obtained from a *Larix* spp. selected from the group consisting of *L. decidua* (European larch), *L. gmelinii* (Dahurian Larch), *Larix kaempferi* (Japanese Larch), *L. sukaczewii* (Russian Larch) or *L. sibirica* (Siberian). There is some controversy about whether *L. sukaczewii* is the same or a different species as *L. sibirica* and it is not listed separately in the Plant List. However, the inventors have now demonstrated that their constituents are indeed different, and so they may be different species. Preferably, the plant extract or the active compound is obtained from *L. kaempferi* or *L. decidua*, with *L. decidua* being the most preferred. Advantageously, *L. decidua* is easily available and comprises high concentrations of the active compounds, and so can be used an optimum source for the extract or active compounds contained therein.

Any part of the *Larix* spp. precursor plant material may be used to form the plant extract, such as the stem, leaves or bark. Preferably, however, bark of the precursor material is used to form the plant extract. Preferably, the precursor material is milled. The extract may be formed by contacting the plant material with a solvent, either at room temperature with agitation, or at an elevated temperature using either microwave or Soxhlet extraction. A suitable solvent may be either dichloromethane (DCM) or methanol. Preferably, the resultant crude extract is separated using chromatography, more preferably gravity column chromatography. A mixture of DCM and methanol may be used to elute the active compounds from the chromatography column. For example, preferably larixyl acetate may be eluted with a mixture of DCM and hexane, preferably 30% DCM/70% hexane. Larixol may be eluted with a mixture of DCM and hexane, preferably 80% DCM/20% hexane. Lariciresinol acetate may be eluted with 100% DCM. Lariciresinol may be eluted with a mixture of methanol and DCM, preferably 5% MeOH in DCM.

Medium pressure flash chromatography or high pressure liquid chromatography (HPLC) may also be used to separate the compounds. Partition chromatography using solvents (for example, ethyl acetate, diethyl ether, hexane, dichloromethane and/or methanol) followed by crystallization of enriched fractions may also be used to purify the compounds.

The inventors have demonstrated that the plant extracts and active compounds are surprisingly useful for treating or preventing an oomycete pathogenic infection. Oomycota or oomycetes form a distinct phylogenetic lineage of fungus-like eukaryotic microorganisms, but they are not fungi per se. They are filamentous, microscopic, absorptive organisms that reproduce both sexually and asexually. Oomycetes occupy both saprophytic and pathogenic lifestyles. They are also often referred to as water moulds. Preferably, infections of *Plasmopara* spp. or *Phytophthora* spp., can be treated or prevented using the compounds, compositions and extracts of the invention. Preferably, *Plasmopara* spp. infections, more preferably *Plasmopara viticola* infections, may be treated or prevented. Preferably, *Phytophthora investans* are treated or prevented.

The oomycetes are some of the most notorious pathogens of plants, causing devastating diseases, including downy mildew, late blight of potato and sudden oak death. Examples of *Phytophthora* infections include late blight on potatoes. Examples of Albuginales infections include white blister rust infections of flowering plants. As such, preferred oomycete pathogen infections, which may be treated with the plant extract or active compound described herein include downy mildew, late blight of potato, ink diseases of European chestnut, and white blister rust infections. Preferably, downy mildew is treated.

The active ingredient, used in the present invention is an effective compound for a variety of diseases such as grape powdery mildew (*Uncinula necator*), grape downy mildew (*Plasmopara viticola*), apple powdery mildew (*Podosphaera leucotricha*), apple scab (*Venturia inaequalis*), apple alternaria blotch (*Alternaria mali*), apple rust (*Gymnosporangium yamadae*), apple blossom blight (*Aclerotinia mali*), pear black spot (*Alternaria kikuchiana*), pear scab (*Venturia nashicola*), pear rust (*Gymnosporangium haraeanum*), peach brown rot (*Sclerotinia cinerea*), peach scab (*Cladosporium carpophilum*), cucurbits powdery mildew (*Sphaerotheca fuliginea*), tomato leaf mold (*Cladosporium fulvam*), eggplant powdery mildew (*Erysiphe cichoracoarum*), grey mold (*Botrytis cinerea*) and *sclerotinia* rot or stem rot (*Sclerotinia sclerotiorum*) on vegetables such as cucumbers, tomatoes, strawberries, and grapes.

Furthermore, the composition of the present invention exhibits a control effect against a disease, such as rice blast; rice sheath blight; cucumber anthracnose; downy mildew of cucumbers, melons, cabbages, Chinese cabbages, onions, pumpkins, grapes; powdery mildew of wheat, barley, cucumbers; blight of potatoes, red peppers, sweet peppers, watermelons, pumpkins, tobaccos, tomatoes; wheat *Septoria* disease; tomato ring spot; citrus melanose; citrus common green mold; pear scab; apple *Alternaria* blotch; onion white tip; watermelon brown rot; various gray mold; various crown rot; various rust. In addition, the composition of the present invention exhibits an excellent control effect against diseases causing by *Plasmodiophora*. More specifically, the composition exhibits an especially excellent control effect against diseases such as blight of potatoes, red peppers, sweet peppers, watermelons, pumpkins, tobaccos, tomatoes; downy mildew of cucumbers, melons, cabbages, Chinese cabbages, onions, pumpkins, grapes; and *Pythium* disease, bacterial shoot blight and leaf blight (brown patch and large patch) of grass.

The oomycete pathogen may infect fruit, for example grapes, apples, strawberries or raspberries. Alternatively, the oomycete pathogen may infect a vegetable.

In order to treat an oomycete pathogen infection, the plant extract or active compound therein is preferably dissolved in a liquid solvent. Suitable solvents include alcohol, acetone or water. In another embodiment, the extract or compound may be provided in an emulsion form. Preferably, the concentration of the active compound in the solvent is about 0.1% to 2% (w/w). The resultant solution or emulsion can then be applied to (e.g. by spraying or dipping) an object which is already infected with an oomycete pathogen, or which is at risk of being infected.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying FIGURES, in which:—

FIG. 1 shows the chemical formulae for embodiments of compounds according to the invention, i.e. (1) larixol ($C_{20}H_{34}O_2$); (2) larixyl acetate ($C_{22}H_{36}O_3$); (3) (+)-lariciresinol ($C_{20}H_{24}O_6$); and (4) (+)-lariciresinol acetate ($C_{22}H_{26}O_7$).

EXAMPLES

Materials and Methods

Extraction of Plant Material

Milled plant samples (0.5 kg each) of the bark of *L. decidua, L. gmelinii, L. sibirica* and *L. sukaczewii*, were extracted with 1 L each of dichloromethane and methanol solvent using a using MARSXpress™ microwave reaction system (voltage: 1600 W, power: 100%, time: 10 min hold: 20 min, temp. 50(DCM)/70(MeOH)° C.). 10-15 g of powdered stem bark was packed into each of 40 vessels. After extraction the solvent was decanted, filtered and evaporated to yield the crude extract. The yields of the crude extracts obtained from these plant samples are shown in Table 1.

TABLE 1

| Yields of crude extracts (% mass/mass) | | |
| --- | --- | --- |
| Plant Species | Dichloromethane extract | Methanol extract |
| L. gmelinii | 1.0% | 9.7% |
| L. sibirica | 1.5% | 6.9% |

TABLE 1-continued

| Yields of crude extracts (% mass/mass) | | |
| --- | --- | --- |
| Plant Species | Dichloromethane extract | Methanol extract |
| L. sukaczewii | 3.6% | 7.3% |
| L. decidua | 1.0% | 9.6% |

*L. kaempferii* was acquired from Alice Holt, Forestry Commission, UK, and compounds were extracted by soaking in dichloromethane at room temperature for 24 h and yielded 0.7% of crude extract (from a 20 kg sample with 40 L of solvent used).

For larger scale extraction, hot extraction using a Soxhlet apparatus was used. 0.8-1 kg of powdered stem bark material was packed into a 5 L Soxhlet apparatus set up over a 5 L flask in a fumehood and allowed to reflux successively with dichloromethane and methanol for 24 h in each case. The solvents were removed and evaporated separately to yield two crude extracts for subsequent chromatographic separation.

Separation of Crude Extracts

The crude extracts obtained above were then separated in the following manner in which the *L. decidua* dichloromethane (DCM) extract is used as an example. The crude extracts (approximately 40-70 g of crude material for each separation) were separated using gravity column chromatography (4 cm diameter column) over silica gel (Merck 9385) using a step gradient starting with 100% hexane, adding DCM in 5% steps until 100% DCM was reached. Then methanol was added in 5% increments until a solvent system of 40% MeOH in DCM was reached. In each case fractions of 75 ml were collected (1 L of hexane, 3 L of dichloromethane and 500 mL methanol were used). By this stage, all compounds of interest had been eluted from the column.

Larixyl acetate was eluted first with 30% DCM/70% hexane, larixol was eluted with 80% DCM/20% hexane, lariciresinol acetate at 100% DCM and lariciresinol at 5% MeOH in DCM.

The methanol extract was also subjected to column chromatography and yielded mainly lariciresinol, but also showed traces of larixol and lariciresinol acetate.

Identification of Compounds

Structures of the extracted compounds were determined using nuclear magnetic resonance spectroscopy ($CDCl_3$, Bruker 500 MHz instrument, mass spectrometry, and optical rotation measurements).

Optical rotations were measured at room temperature in chloroform (1, 2, 3)/methanol (4) using a JASCO P-1020 polarimeter using a cell with a path length of 0.1 dm.

Nuclear Magnetic Resonance spectroscopic experiments were performed on a 500 MHz Bruker AVANCE NMR spectrometer. The spectra were recorded in deuteriochloroform ($CDCl_3$) and methanol-$d_4$ ($CD_3OD$) and the chemical shifts were recorded in ppm (parts per million) relative to the solvents. The deuteriochloroform was referenced according to the central line at δ 7.260 in the $^1H$ NMR spectrum and at δ 77.23 in the $^{13}C$ NMR spectrum, whereas the methanol-$d_4$ was referenced according to the central line at δ 4.87 in the $^1H$ NMR spectrum and at δ 49.15 in the $^{13}C$ NMR spectrum.

The low resolution electron impact mass (GC-MS) spectra were acquired using a Hewlett Packard G1800A GCD system and the LCMS analysis were recorded on a QTOF Premier—Water Corp. instrument through direct infusion at 10 μl/min.

Results and Discussion

Referring to FIG. 1, there are shown the structural formulae of four key compounds found in each of the plant extracts.

Compound 1 is larixol; Compound 2 is larixyl acetate, which is the naturally occurring acetate derivative of compound 1; Compound 3 is (+)-lariciresinol (NSC 329247); and Compound 4 is (+)-lariciresinol acetate, which is the naturally occurring acetate derivative of compound 3.

The yields of each of these compounds from the various plant samples is summarised in Table 2 in which "% m/m" is mass of sample per 100 g of dried plant material. For *L. kaempferii* results are reported as % m/m of compound in crude extract.

TABLE 2

Preliminary investigations of yields of compounds

| Plant species | Compound | % mass/mass |
|---|---|---|
| *L. gmelinii* | larixol | 0.5% |
| | larixyl acetate | 1.5% |
| | lariciresinol | Trace |
| | lariciresinol acetate | Trace |
| *L. sibirica* | larixol | Trace |
| | larixyl acetate | Trace |
| | lariciresinol | 1.9% |
| | lariciresinol acetate | 0.7% |
| *L. decidua* | larixol | 0.8% |
| | larixyl acetate | 0.2% |
| | lariciresinol | 0.1% |
| | lariciresinol acetate | Trace |
| *L. kaempferii* | larixol | 0.99% of crude extract |
| | larixyl acetate | 1.60% of crude extract |
| | lariciresinol | Trace |
| | lariciresinol acetate | Trace |
| *L. sukaczewii* | larixol | Trace |
| | larixyl acetate | Trace |
| | lariciresinol | Trace |
| | larisiresinal acetate | Trace |

The preliminary screening results and activities of the compounds are summarised in Table 3.

TABLE 3

Preliminary Screening Results

| Sample (% mass/volume) | Activity |
|---|---|
| Crude extracts *Larix decidua* | |
| Dichloromethane extract 0.1% | 90.2% |
| Dichloromethane extract 0.01% | No activity |
| Methanol extract 0.2% | 13.3% |
| Methanol extract 0.02% | No activity |
| Crude extracts *Larix sukaczewii* | |
| Dichloromethane extract 0.1% | 98.3% |
| Dichloromethane extract 0.01% | No activity |
| 1. larixol | |
| 0.147% | 99.5% |
| 0.074% | 100% |
| 0.0147% | 36.3% |
| 2. larixyl acetate | |
| 0.12% | 100% |
| 0.012% | 69.2% |
| 3. (+)-lariciresinol | |
| 0.1% | 94.1% |
| 0.01% | 14.4% |
| 4. (+)-lariciresinol acetate | |

TABLE 3-continued

Preliminary Screening Results

| Sample (% mass/volume) | Activity |
|---|---|
| 0.08% | 92.4% |
| 0.036% | 78.8% |
| 0.008% | 13.1% |
| Control (Kocide Opti-Copper reference) | |
| 0.1% | 97.3% |
| 0.01% | 80.2% |

Further Screening Results

The inventors tested the activities of a number of compositions comprising various concentrations of the active compounds, as set out in Table 4, against different oomycetes, *P. viticola* and *P. infestans*.

TABLE 4

Compositions comprising the active isolates

| Substance | Code | Efficacy (%) | Concentration (% mass/volume) | Solvent |
|---|---|---|---|---|
| Larixyl acetate | LD-SURR-001 | 99.5 | 0.147% | Isopropanol |
| | | 100.0 | 0.12% | Ethanol |
| | | 99.9 | 0.1% | Ethanol |
| | | 99.4 | 0.1% | Ethanol |
| | | 98.4 | 0.05% | Ethanol |
| | | 83.3 | 0.025% | Ethanol |
| | | 69.2 | 0.012% | Ethanol |
| | | 24.5 | 0.01% | Isopropanol |
| Larixol | LD-SURR-002 | 99.5 | 0.147% | Isopropanol |
| | | 98.8 | 0.1% | Ethanol |
| | | 100.0 | 0.074% | Isopropanol |
| | | 91.2 | 0.025% | Ethanol |
| | | 36.3 | 0.0147% | Isopropanol |
| Lariciresinol acetate | LD-SURR-003 | 88.8 | 0.1% | Ethanol |
| | | 92.4 | 0.08% | Ethanol |
| | | 78.8 | 0.04% | Methanol |
| | | 78.4 | 0.025% | Ethanol |
| | | 13.1 | 0.008% | Ethanol |
| Lariciresinol | LD-SURR-004 | 93.3 | 0.1% | Ethanol |
| | | 94.1 | 0.1% | Ethanol |
| | | 86.5 | 0.1% | Ethanol |
| | | 56.9 | 0.052% | Methanol |
| | | 64.6 | 0.025% | Ethanol |
| | | 14.4 | 0.01% | Ethanol |
| | | -4.9 | 0.01% | Ethanol |
| Kocide (copper reference) | | 92-99% | 0.10% | |
| | | 63-96% | 0.01% | |

TABLE 5

Preliminary results and activities of the compounds against *P. viticola* (zoospore germination and activity) and *P. infestans* (germination) in vitro

| Sample code | Sample composition | Minimal inhibitory concentration (MIC(100%)) *Plasmopara viticola* | Minimal inhibitory concentration (MIC(100%)) *Phytophthora infestans* |
|---|---|---|---|
| DCM-Extract T | Dichlormethane extract from bark | 250 ppm | No activity |
| MeOH Extract (1) | DCM extract and sequential methanol extract | 125 ppm | 63 ppm |
| MeOH Extract (2) | Methanol extract from bark | 250 ppm | 125 ppm |
| LD-SURR-001 | Larixyl acetate | 4 ppm | 125 ppm |
| LD-SURR-002 | Larixol | 16 ppm | 500 ppm |

TABLE 5-continued

Preliminary results and activities of the compounds against *P. viticola* (zoospore germination and activity) and *P. infestans* (germination) in vitro

| Sample code | Sample composition | Minimal inhibitory concentration (MIC(100%)) *Plasmopara viticola* | Minimal inhibitory concentration (MIC(100%)) *Phytophthora infestans* |
|---|---|---|---|
| LD-SURR-003 | Larisciresinol acetate | 125 ppm | No actvity |
| LD-SURR-004 | Larisciresinol | 250 ppm | No activity |

CONCLUSIONS

The crude extracts of each of the *Larix* species and also the four compounds from *Larix* (two closely related diterpenoids and two related lignans), were found to be active in the laboratory against the oomycete *Plasmopara viticola*, i.e. the downy mildew-causing pathogen, and also *Phytophthora investans*, i.e. causes potato blight. The inventors have found these compounds to be present in varying amounts depending on species and site of collection from a variety of larch species: *Larix sibirica* (Siberian), *Larix decidua* (European larch), *Larix gmelinii* (Dahurian Larch), *Larix sukaczewii* (Russian Larch) and *Larix kaempferi* (Japanese Larch). They therefore have demonstrated that the extracts and compounds are surprisingly useful for treating or preventing any oomycete pathogenic infection.

The work leading to this invention has received funding from the European Union Seventh Framework Programme (FP7-KBBE-2008-2B) under grant agreement no 227239.

That which is claimed is:

1. A method of treating grape downy mildew infection in grapes in need thereof, the method comprising administering to said grapes a therapeutically effective amount of a *Larix* extract selected from the group consisting of *Larix decidua*, *Larix gmelinii*, *Larix kaempferi*, *Larix sukaczewii* and *Larix sibirica*,
wherein said grapes are effectively treated for the downy mildew infection by the *Larix* extract.

2. The method of claim 1, wherein the *Larix* extract comprises larixol or lariciresinol, or an active derivative thereof.

3. The method of claim 2, wherein the active derivative of larixol or lariciresinol comprises a labdane diterpenoid, a lignan, or a synthetic derivative of any of the aforementioned compounds.

4. The method of claim 3, wherein said synthetic derivative is an ester derivative, an heterocyclic derivative, a derivative derived by alkylation or oxidation, or an acetate derivative of larixol or lariciresinol.

5. The method of claim 2, wherein the active derivative of larixol or lariciresinol comprises larixyl acetate or lariciresinol acetate.

6. The method of claim 1, wherein the *Larix* extract is obtained from *L. kaempferi* or *L. decidua*.

7. The method of claim 1,
wherein the *Larix* extract is formed by contacting *Larix* plant material with a solvent, either at room temperature with agitation, or at an elevated temperature using either microwave or Soxhlet extraction,
wherein the solvent is optionally either dichloromethane (DCM) or methanol, and
wherein the *Larix* extract is separated using chromatography.

8. The method of claim 1, wherein the *Larix* extract is dissolved in a liquid solvent selected from alcohol, acetone or water.

9. The method of claim 1, wherein the *Larix* extract is provided in an emulsion form.

* * * * *